(12) United States Patent
Skaling et al.

(10) Patent No.: US 6,632,534 B2
(45) Date of Patent: *Oct. 14, 2003

(54) ENCASED TIME DOMAIN REFLECTOMETRY PROBE

(75) Inventors: Whitney Skaling, Buellton, CA (US); Laszlo Rudolics, Santa Barbara, CA (US)

(73) Assignee: Soilmoisture Equipment Corp., Goleta, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/944,538

(22) Filed: Aug. 30, 2001

(65) Prior Publication Data

US 2003/0118832 A1 Jun. 26, 2003

(51) Int. Cl.[7] .......................... B32B 27/00; G01N 22/00
(52) U.S. Cl. .................... 428/412; 428/411.1; 428/413; 428/416; 324/534; 324/600; 324/601; 324/632; 324/642; 324/643
(58) Field of Search .............................. 428/411.1, 412, 428/413, 416

(56) References Cited

U.S. PATENT DOCUMENTS

| | | | | |
|---|---|---|---|---|
| 4,174,498 A | * | 11/1979 | Preikschat | 324/670 |
| 5,136,249 A | * | 8/1992 | White et al. | 324/632 |
| 5,420,517 A | * | 5/1995 | Skaling et al. | 324/534 |
| 5,554,936 A | * | 9/1996 | Mohr | 324/446 |
| 5,646,537 A | * | 7/1997 | Skaling et al. | 324/601 |
| 5,723,979 A | * | 3/1998 | Mohr | 324/446 |

FOREIGN PATENT DOCUMENTS

| | | | |
|---|---|---|---|
| EP | 0 297 604 A2 | * | 1/1989 |
| EP | 0 585 691 A1 | * | 3/1994 |
| GB | 2 213 596 A | * | 8/1989 |
| WO | WO 97/09590 | * | 3/1997 |
| WO | WO 98/25109 | * | 6/1998 |

* cited by examiner

Primary Examiner—P. Hampton-Hightower
(74) Attorney, Agent, or Firm—Lyon & Harr, LLP; Richard T. Lyon; Katrina A. Lyon

(57) ABSTRACT

A probe adapted for use with a time domain reflectometry device in primarily measuring the moisture content in soils and other mediums. This probe can however be used in may differing measurement applications involving materials of specific dielectric constants as well as apparent dielectric constants that are derived from a matrix of several differing dielectrics. In the probe according to the present invention, the inner core of the probe is composed of an inner conductive element, a conductor that is used to transmit a broadband pulse. A dielectric liquid, solid or gel surrounds this inner conductive core, and assists in retaining broadband signal strength. The dielectric material is then encased in a metallic outer shell that serves as a protective housing for the probe. This outer shell is electronically transparent to the electromagnetic pulse transmitted by the active inner conductive core and surrounding dielectric. The outer shell is preferably made of stainless steel, but can be made of other materials as they serve to protect the inner dielectric material and conductive core. This combination of features allows a broadband pulse transmitted through the probe to penetrate into the material being measured, returning a much larger reflection feature upon reaching probe end points, while protecting the dielectric-coated transmission elements inside.

22 Claims, 8 Drawing Sheets

(8 of 8 Drawing Sheet(s) Filed in Color)

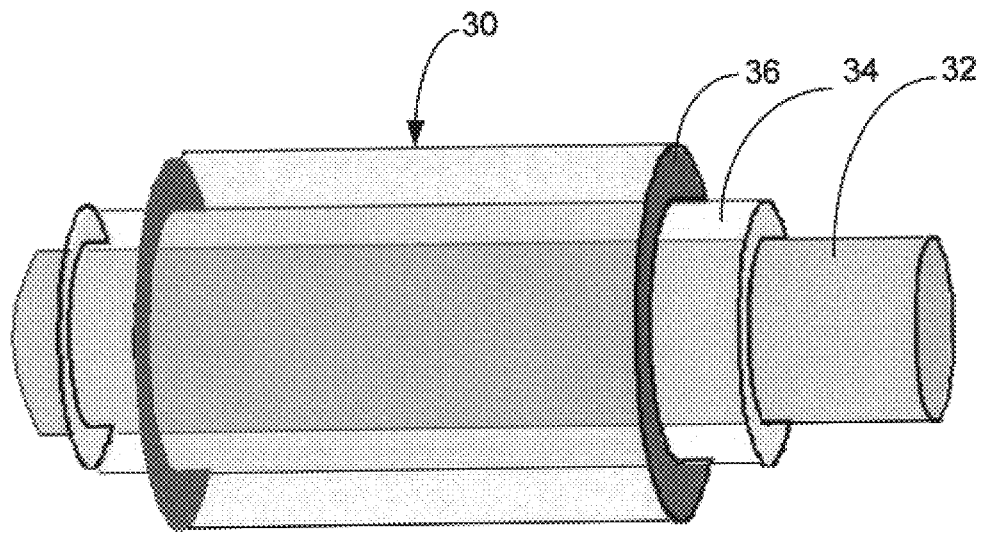
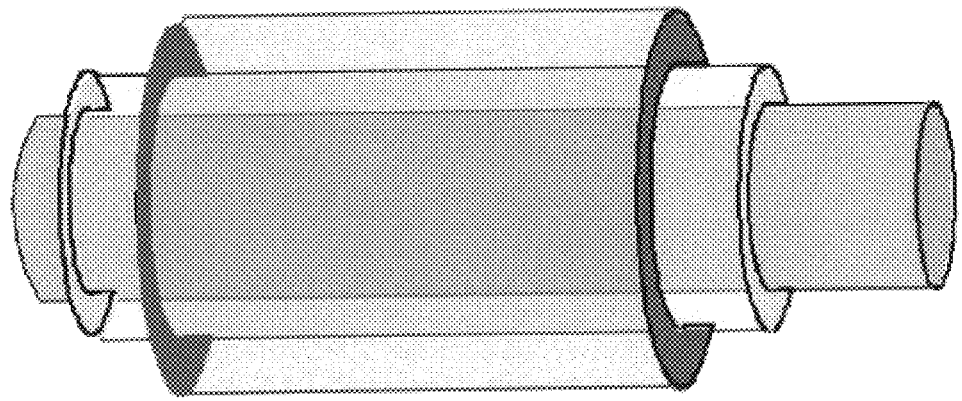
FIG. 3

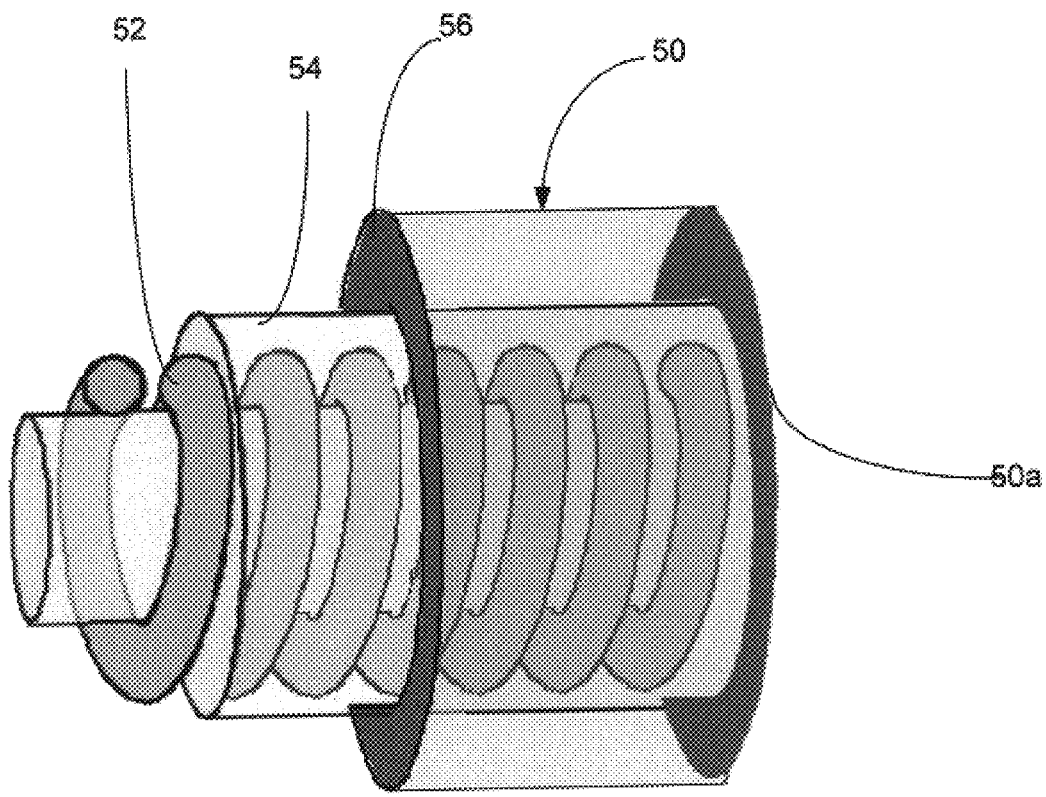
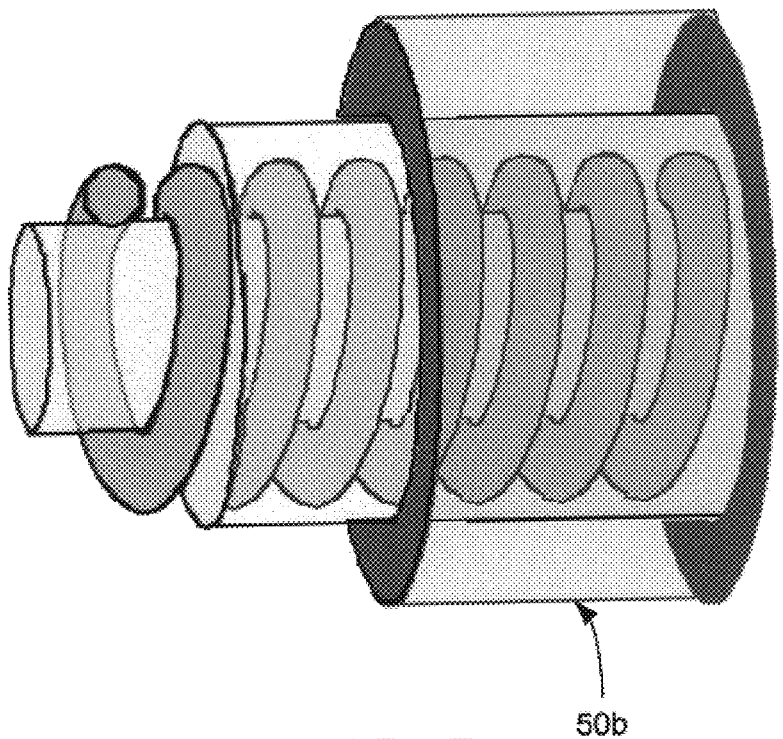
FIG. 5

ENCASED TIME DOMAIN REFLECTOMETRY PROBE

BACKGROUND OF THE INVENTION

1. Technical Field

This invention relates generally to a probe adapted to measure the dielectric properties of soil and other materials. More specifically, this invention relates to a probe for measuring the moisture content of soil or other medium.

2. Background Art

In the past, there have been a number of instruments used to measure the moisture content in soil so that farmers, ranchers, conservationists and the like could determine when to irrigate crops, plants, trees, etc. Early devices included taking bore samples of soil and placing the samples in devices that would measure the amount of moisture content in the soil. These devices generally required time-consuming oven-drying processes to determine the moisture content. The time delays, sometimes taking several days to characterize the moisture content of the soil, resulted in crops being either over- or under-irrigated for periods of time. As a result, crop damage or quality loss was a common occurrence.

Other soil moisture measuring devices, such as neutron source back scatter devices have also been used to measure soil moisture. These devices are bulky to transport to the field where soil measurements are typically taken and they rely on radioactive elements. These radioactive devices often are costly, require specialized personnel to operate, and have to be calibrated in the field prior to use at each measurement site.

In contrast to the prior art described above, more recent moisture measuring devices have been devised which operate on the principles of Time Domain Reflectometry (TDR). Geologists and others have long recognized a relationship between the dielectric properties of soil, rock and other materials, and their moisture content. However, they initially lacked the instrumentation necessary to make full use of this knowledge. Time Domain Reflectometry, largely developed as the result of World War II radar research, offered a method to define these dielectric relationships. With the advent of commercial TDR research oscilloscopes in the early 1960s, it became feasible to test this new technology. Today, TDR technology is the "cutting edge" methodology for many diverse applications including the determination of basic soil water and material/water relationships.

TDR systems utilize the principle of TDR in order to convert the travel time of a broadband, electromagnetic pulse into volumetric water content. In practice these TDR systems generate a fast-rise pulse and send it at the speed of light down a transmission line consisting of at least two parallel wave guides or a coaxial arrangement of probes that are inserted or buried in the soil or other material to be measured. The velocity of propagation of the broadband pulse (often that incorporates frequencies that exceed 3 GHz) in soil is determined primarily by its water content. The pulse is reflected from the open ends of the wave guides/probes and returns along the original path. By microprocessor or other computing device, the travel time of the pulse is used to calculate the apparent dielectric constant of the soil. The actual digitized TDR wave form created as the pulse progresses down the wave guides can be displayed on a high resolution graphic LCD display for storage and interpretation. The actual time delay and correlated volumetric water content may also be digitally displayed on the screen.

TDR systems eliminate the need for using nuclear based instrumentation and the associated radiation, health and safety hazards. These systems eliminate site-specific calibration and the requirement for costly, specialized licensed personnel associated with neutron probes. They also provide auto logging capabilities that are not practical with nuclear techniques.

In the past, probes used with TDR systems have been manufactured having an inner conductive core that is surrounded by a dielectric material. This thin dielectric layer between the transmission element and the material being measured retains and reflects some of the energy along the transmission element as the pulse progresses from start to endpoint within the probe. This dielectric layer is key as it provides for a high coefficient of reflection that is necessary for the determination of the probe's end points in highly conductive materials such as saline water, or conductive particle mixtures. This determination of these endpoints is used in the calculations to determine the apparent dielectric constant of the material being measured. For some measurements in high conductivity materials, end point reflections are attenuated to an insignificant level, undetectable by waveform analysis. In such cases, the high coefficient of reflection provided by the dielectric layer surrounding the inner conductive core is absolutely necessary to obtain accurate TDR measurements.

Although the dielectric layer provides for a high coefficient of refection, one problem with having the outer layer being made of soft or brittle dielectric materials is that it wears, scratches or breaks during multiple insertions into the ground or other material where the moisture is to be measured. This is particularly true when the probe is used to measure the moisture content of hard or abrasive soils, since the probes are typically repeatedly inserted in the soil to obtain the desired measurements. Additionally, the outer dielectric material is often difficult to manufacture such that an even layer is achieved. When the outer layer of dielectric is worn uneven, scratched or is unevenly manufactured the dielectric properties, and therefore the accuracy of the probe, is degraded.

Therefore, what is needed is a TDR probe that is immune to wear and scratching of the dielectric material coating the inner conductive element and that is easily manufactured to achieve reliable and consistent dielectric measurement results.

SUMMARY

The system and process of the present invention satisfies all of the foregoing needs. The system and process provides a wave guide-like structure or probe (usually used in pairs or sets) that can be used for measuring the moisture content of soil or other materials. Probes according to the present invention, using the techniques described herein, can also be used in the following measurement areas:

(1) determination of concentrations of particles suspended in water and other liquids;
(2) determination of the amount of air entrapped in liquids, slurries and gels;
(3) determination of the liquid levels of immiscible fluids having differing dielectric character;
(4) determination of the proportional content in differing dielectrics soluble in water; and
(5) determination of the bulk content of the material being measured.

In the probe according to the present invention, the inner core of the probe is composed of an inner metallic element. This metallic element is a conductor that is used to transmit a broadband pulse. A dielectric liquid, solid or gel surrounds this inner conductive core, and assists in retaining broadband signal strength. The outer dielectric material is then encased in an outer shell that serves as a protective housing for the probe. This outer shell is preferably made of stainless steel, but can be made of other conductive materials as they serve to protect the inner dielectric material and metallic core. This combination of features allows a pulse transmitted through the probe to penetrate into the material being measured, while protecting the dielectric-coated transmission elements. Only the inner conductive elements (conductor and dielectric layer) are active and electrically connected to the components of the TDR system. Since the outer shell is not electrically connected in any manner to the transmission elements it simply acts as a tough and effective housing that protects a "dielectrically-coated" transmission element. This invention combines the need for a dielectric coating on the transmission element and strong outer covering into a single assembled unit that provides both protection for multiple insertions into abrasive or in highly corrosive materials while allowing maximum signal retention for end point reflection determination.

The probe of the system and method according to the present invention, which is typically used as a pair or in sets, allows for the broadcasting of pulsed energy between the probes to migrate through the material being measured as well as along the dielectric-coated transmission elements of the probes. The net result is a much greater reflected energy from the pulse as it reaches the end points of the probes. This high coefficient of reflection from the pulse reaching the probe endpoint is instrumental in determining accurate and repeatable time determinations for speeds of propagation through the material being measured by the pair or set of probes. The probe according to the present invention is effective because it retains certain pulse energy and frequencies both in the continuous distributed dielectric coating and the transmission element making it an apparent continuous capacitive element to lower frequencies within the broadband pulse. As a result, more energy is stored in this dielectric layer and available to be reflected when the pulse reaches the endpoint of the probe.

One issue of note is that the travel time of a transmitted pulse using the encased probe of the present invention will be distorted because a portion of the pulse signal travels the probe interior while the greater portion travels more slowly between sets of probes (in the material being measured). This effect tends to shorten the travel times being measured when compared to probes without any dielectric coating. To adjust for this issue, a lookup table must be created that properly equates shortened travel times derived from the probe of the present invention to the actual dielectric constants of the materials being measured. Such a lookup table can be created by using the probe of the present invention to take measurements of travel times and speed of propagation of an electromagnetic pulse and associated reflection in various materials and then determining the moisture content, liquid levels, concentrations, and so on. Once this table is generated it can be used for future measurements to determine the moisture content, liquid levels, and concentrations that correspond to each range of subsequently-measured travel times.

The method of operation of the probe of present invention is relatively simple. A broadband pulse is transmitted from a pulse generator down coaxial transmission lines or cables to the probe or probes. The signal travels the length of the inner conducting element. In doing so, some of the pulse energy is broadcast through the dielectric layer, and then through the outer protective shell into the material being measured. Some of the energy is captured in the dielectric layer, increasing the speed of the signal as it is propagated down the inner conducting element. The remainder of the signal is broadcast through the dielectric and outer shell out into the material being measured. Due to an impedance mismatch where the coaxial cable and the probes are joined, a downgoing beginning reference point, a TDR wave form feature, is produced. The beginning reference point provides a starting point for measuring the accumulated time delay as the electronic pulse continues to travel through the probe. An ending reflection point, a TDR wave form feature, is created as the electronic pulse reaches the end of the probe and transmits into the surrounding soil. Upon reaching the probe end point there is ample signal strength to indicate a reflected end point. This reflected end point is the result of a complex interaction between a portion of the broadband pulse frequencies and energies that travel through the inner conducting elements of each individual probe, and the portion of the broadband pulse frequencies and energies that travel between two or more of the probes as well as through the material being measured. The apparent dielectric of the soil may be ascertained having determined the accumulated delay time, and in turn one can ascertain the moisture content of the soil using the apparent dielectric value. Once the travel times are known the moisture content of the material can be determined by utilizing a look up table common in TDR techniques as was discussed above.

In many cases it is necessary to make measurements in high loss materials that are abrasive and/or corrosive. The low loss probe of the present invention has shown an ability to both provide a tough, protective, outer surface to protect the inner workings of the probe for multiple insertions in abrasive materials such as soils, while providing ample signal for noticeable and detectable endpoints in high loss materials being measured. High loss materials being measured can be soils (intermixed materials), slurries, or gels, whose water contains high salinity content, or electrically conductive particles that diminish the broadcasting ability of the broadband signal between probe pairs being used to make material measurements.

The probe of the present invention can have different configurations. For instance, one embodiment of the probe is rod-shaped. This rod-shaped probe has a rod-shaped conducting element. Surrounding this conducting element is a layer of dielectric material. An outer protective shell surrounds the dielectric layer and conducting element in a concentric manner. The rod-shaped probe embodiment can have a cone-shaped pointed tipped to make it easier to insert it into soil or other material being measured. Additionally, this rod-shaped probe can be of different lengths and diameters.

Another embodiment of the probe of the present invention entails a disc-shaped probe. A pair of these disc-shaped probes can be configured to align along a common axis, such that a circular hole through each disc is aligned in parallel and can be mounted on some sort of axle or chassis that can be attached to a tractor or other vehicle. The discs can then be forced into the ground so that measurements can be taken while the vehicle is moving. The inner core of each disc-shaped probe is a conducting element. A dielectric material is sandwiched between the conducting element and an outer shell.

It has been found that more precise readings can be obtained using TDR techniques when a longer effective conductor length exists (resulting in longer travel times of the aforementioned electromagnetic pulse) in the probes being used to take the measurement. Another embodiment of the present invention uses this principle to employ a coil-shaped conductor within a rod-shaped probe. In this embodiment, a coil-shaped conductor is potted within a dielectric material. An outer protective shell surrounds the combination of the coil-shaped conductor and the dielectric material. Through the use of the coil-shaped conductor the effective length of the conductor is increased over what can typically be found in a probe of similar length that employs a straight conductive member, thus improving the accuracy of the probe(s).

In yet another embodiment of the present invention, a pair of probes is concentrically or coaxially-configured. The inner probe is rod-shaped, having an inner conducting element that is covered with a dielectric layer. An outer protective shell encases both the inner conducting element and the dielectric layer of this probe. A ring-shaped probe surrounds the rod-shaped probe, with the two probes being concentrically located, but separate. The ring-shaped probe also has an inner conducting element that is surrounded by a dielectric layer. An outer protective shell encases both the inner conductor and the dielectric layer of the ring-shaped probe. In use, the material to be measured in situated between the two probes such that the material is lodged between the two probes.

In another embodiment of the probe of the present invention, the probe is plate-shaped. This probe has a plate-shaped inner conductive element that is surrounded by a dielectric layer. The dielectric layer is encased in a protective outer shell. In use, two plate-shaped probes can be configured such that they are parallel to each other and the material to be measured flows between them, along the larger surfaces of the probes. However, these probes can also be configured such that they are closer to each other at one end and are further apart at the other end. This configuration might typically be used in a mixer or bulk transfer systems where material flows between the probes and differing densities of the material to be measured may make it difficult to get accurate readings. Angling the probes relative to each other in this manner increases the density of the material to be measured as it is compressed between the probes where the probes are least separated in distance. This increased density of the measured material allows for more accurate and consistent measurements of the dielectric properties of the materials. It should also be noted that the plate-shaped probes in this embodiment do not necessarily have to be flat. These probes could be curved if desired. Additionally, these plate-shaped probes do not have to be rectangular in shape. For instance, they could be circular, triangular or configured in any type of geometric cross-sectional shape.

In yet another embodiment of the probe of the present invention, a longer conductor is embedded within a plate-shaped probe. The longer conductor is a snake-like element encased in a dielectric material. The inner conductor and dielectric material are covered by an outer protective shell. Again, as discussed in the embodiment above, these probes can be angled toward each other and can also be of different shapes (e.g., rectangular, circular, triangular, octagonal, etc.)

The probe of the present invention can be made of various materials. The inner conductive element is made of a conductive material, typically a metal such as stainless steel or copper, for example. The dielectric layer that surrounds the inner conductive element of the probe of the present invention can take the form of solid, liquid or gel. Typically the dielectric layer is, for example, a hardenable epoxy of known dielectric constant. The outer protective shell is typically made of stainless steel, but could equally well be made of other suitable material.

DESCRIPTION OF THE DRAWINGS

The file of this patent contains at least one drawing executed in color. Copies of this patent with color drawing (s) will be provided by the U.S. Patent and Trademark Office upon request and payment of the necessary fee.

The specific features, aspects, and advantages of the present invention will become better understood with regard to the following description, appended claims, and accompanying drawings where:

FIG. 3 is cut-away view of two rod-shaped probes of the present invention.

FIG. 5 is a cutaway view of two probes of the present invention wherein a coil-shaped conductor is employed in a rod-shaped probe.

DETAILED DESCRIPTION OF THE PREFERRED EMBODIMENTS

In the following description of the preferred embodiments of the present invention, reference is made to the accompanying drawings which form a part hereof, and in which is shown by way of illustration specific embodiments in which the invention may be practiced. It is understood that other embodiments may be utilized and structural changes may be made without departing from the scope of the present invention.

Probe Overview

Figure 1:
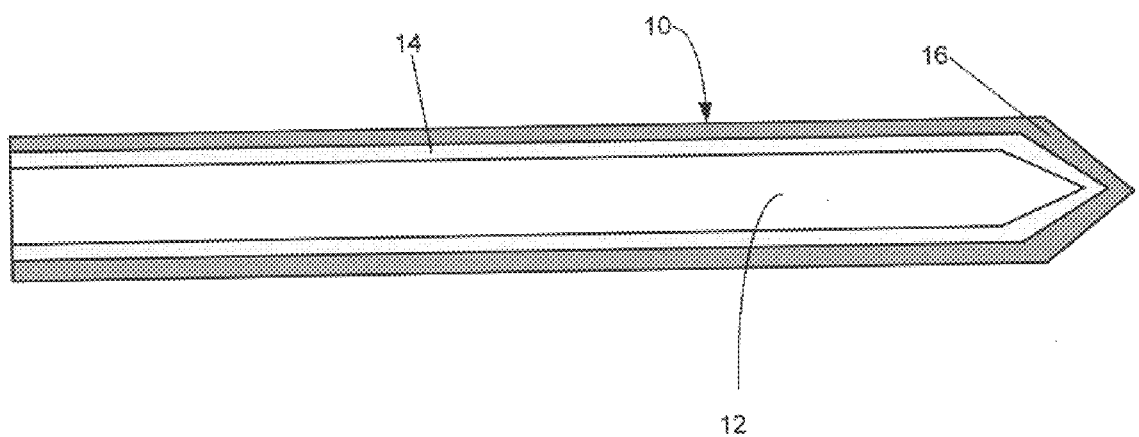
FIG. 1 is cut-away side view of one embodiment of the probe of present invention.

Turning now to FIG. 1, there is shown one embodiment of the probe 10 (or antenna or wave guide) of the present invention. The inner core 12 of probe 10 is an inner conducting element preferably made of stainless steel or other electrically-conductive material. This inner conducting element 12 is electrically active and used as a transmission element. The inner conducting element 12 is connected to a pulse generator via a coaxial cable (not shown) that is typically used in a TDR system. A dielectric layer 14 of the probe 10, is constructed from a hardened epoxy or other dielectric plastic material, and surrounds the inner conducting element 12. Surrounding the dielectric layer 14 is an outer protective shell 16 of the probe 10. This outer shell 16 is preferably made of stainless steel.

Concept of Operation

Figure 2:
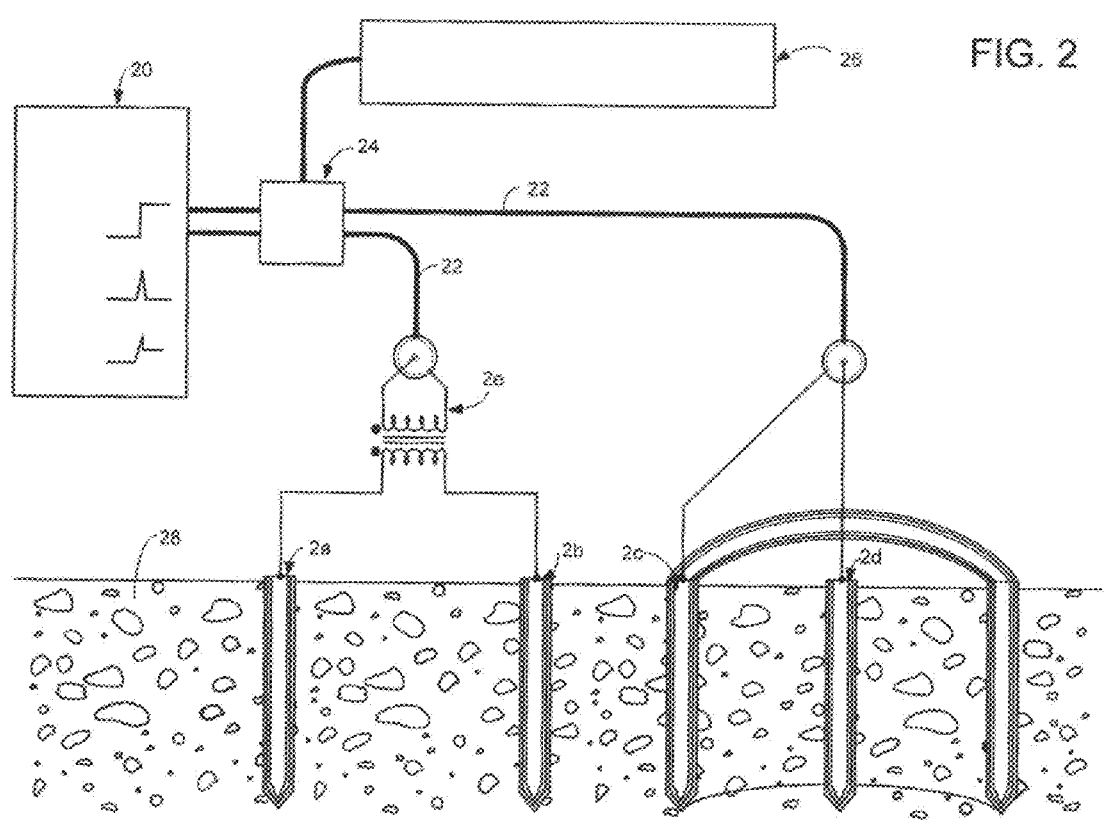
FIG. 2 is a schematic showing how the probes of the present invention are used to measure the dielectric properties (via the measurement of travel times of an electromagnetic pulse) of material in a typical Time Domain Reflectometry Measurement system.

As shown in FIG. 2, the probe of the present invention is typically used in pairs 2a, 2b in a "balanced" TDR measurement configuration or coaxial arrangements 2c, 2d for "unbalanced" TDR measurement configurations. Balanced measurements use a small pulse transformer 2e known as a "balun", unbalanced measurements do not. In general, the probes are inserted into the soil to determine the apparent dielectric constant of the soil or other material being measured by determination of travel times through the material. It is known that the velocity of propagation through a medium is proportional to the square root of the dielectric of the medium. When the probes are inserted in soil, the soil, together with the probes, act as an electronic circuit. The transmission speed of a broadband pulse in the probes is affected primarily by the water content of the soil or other material being measured. As water content increases in the soil or other measured material, so also does the travel time of the pulse reaching a reflected end point from the probe beginning. The average travel time from beginning to end as observed in TDR wave form features will determine the apparent dielectric of the material being measured. Thus, there is a relationship between the apparent measured dielectric constant and the moisture content of the measured material. Hence, once the apparent dielectric constant is determined from propagation velocity, the volumetric soil moisture can be computed or deduced.

One way of deducing soil moisture is to employ a processor that identifies the beginning and end point wave form features from a digitized TDR waveform and from these features determines the average travel time. A lookup table is then used to ascertain the moisture content given the average travel time. The lookup table is keyed to the type of probes being employed for the measurements as well as the type of material being measured. For a given moisture content the material associated with a lookup table will exhibit a particular apparent dielectric constant. As indicated earlier, the apparent dielectric constant can be established for a particular material by knowing the propagation velocity of the pulse. Since the propagation velocity is defined by the average travel time and the dimensions of the probe, the travel time is all that is needed to establish the moisture content of the material being measured. Thus, a moisture value for a measured average travel time can be read directly from the table. However, other techniques to determine soil moisture from the soil dielectric constant may be employed by the present invention.

More specifically, referring to FIGS. 1 and 2, the method of operation of the probe of present invention is relatively simple. A broadband pulse, stepped, impulse, or a combination pulse is transmitted from a pulse generator 20 through a digitizer 24 connected to a microprocessor or other computing device 26, down coaxial transmission lines or cables 22, to the probe set 2a, 2b, a pair, that can be placed at various distances from one another, or to 2c,2d, a coaxial pair (center probe and ring), the center probe and ring having various diameters. Both pair types are inserted in the material to be measured 24. The signal travels the length of the inner conducting element 12. In doing so, some of the pulse energy is broadcast through the dielectric layer 14 of the probes pairs 2a, 2b or 2c, 2d, and then through the outer shell 16 into the material being measured. Some of the energy is captured in the dielectric layer, increasing the speed of the signal as it is propagated down the inner conducting element. The remainder of the signal is broadcast through the dielectric and outer shell out into the material being measured. Due to an impedance mismatch where the coaxial cable and the probes are joined, a downgoing beginning reference waveform feature in the digitized TDR waveform is produced. The beginning reference waveform feature provides a starting point for measuring the accumulated time delay as the electronic pulse continues to travel through the probe assembly. An ending reflection waveform feature in the TDR wave form is created as the electronic pulse reaches the end of the probe assembly producing a large reflection feature as the pulse enters the surrounding soil. The apparent dielectric of the soil may be ascertained having determined the accumulated delay time, and in turn one can ascertain the moisture content of the soil using the apparent dielectric value. Once the dielectric properties are known, the moisture content of the material can be determined by utilizing a predetermined lookup table.

One issue of note is that the measured travel time of the pulse using the probe of the present invention is shorter when compared to probes without any dielectric coating. To adjust for this, a lookup table must be created that properly equates the shortened travel times for this probe to the actual dielectric constants of the materials being measured. Such a lookup table can be created by using the probe of the present invention to take measurements of a pulse's travel times and speed of propagation in various materials and then determining the moisture content of these materials that correspond to each dielectric measurement via conventional techniques. Once the table is generated it can be used for subsequent measurements to determine the moisture content that corresponds to each range of subsequently measured travel times.

Probe Configurations

The improved probe of the present invention can have different configurations. For instance, as shown in FIG. 3, one embodiment of the probe 30 is rod-shaped. This rod-shaped probe 30 has a rod-shaped conducting element 32. Surrounding the tubular conducting element 32, is a layer of dielectric material 34. The outer protective shell 36 surrounds the dielectric material 34 and conducting element 32 in a concentric manner. The rod-shaped probe 30 of this embodiment can have a cone-shaped pointed tipped (like that shown in FIG. 1) to make it easier to insert it into soil or other material being measured.

Figure 4:
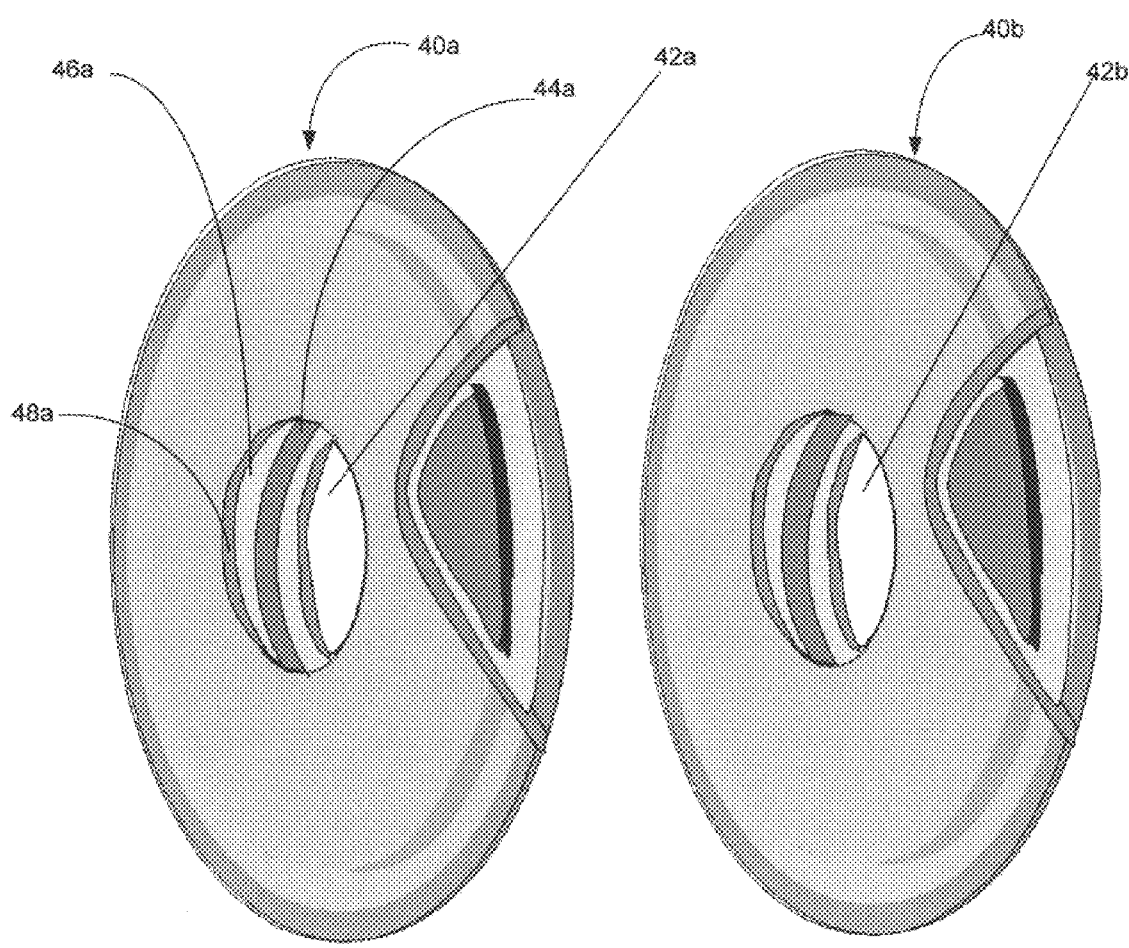
FIG. 4 is a cutaway view of two disc-shaped probes of the present invention.

Another embodiment of the probe of the present invention is shown in FIG. 4. This embodiment entails a disc-shaped probe 40. A pair of these disc shaped probes 40a and 40b can be configured to align along a common axis, such that a circular hole 42a, 42b through each disc is aligned in parallel and the probes can be mounted on an axle or chassis. The inner core of each disc-shaped probe 40 is a conducting element 44a, made of some conducting material. A dielectric material 46a is sandwiched between the conducting element 44a and an outer shell 48a. Such a probe configuration can be attached to a tractor or other vehicle. In this manner, the probes can thus be forced into the material to be measured such that readings can be taken while the vehicle is moving.

It has been found that more precise readings can be obtained using TDR techniques when a longer effective conductor length exists in the probes being used to take the measurement. Another embodiment of the present invention 50 uses this principle to employ a coil-shaped conductor within a rod-shaped probe. In this embodiment of the probe 50, shown in FIG. 5, a coil-shaped conductor 52 is potted within a dielectric material 54. An outer protective shell 56 surrounds the coil-shaped conductor 52 and the dielectric material 54. The probe is again typically used in pairs 50a, 50b. Through the use of the coil-shaped conductor 52 the effective length of the conductor is increased over what typically be found in a probe of similar length that employs a straight conductive member.

Figure 6:
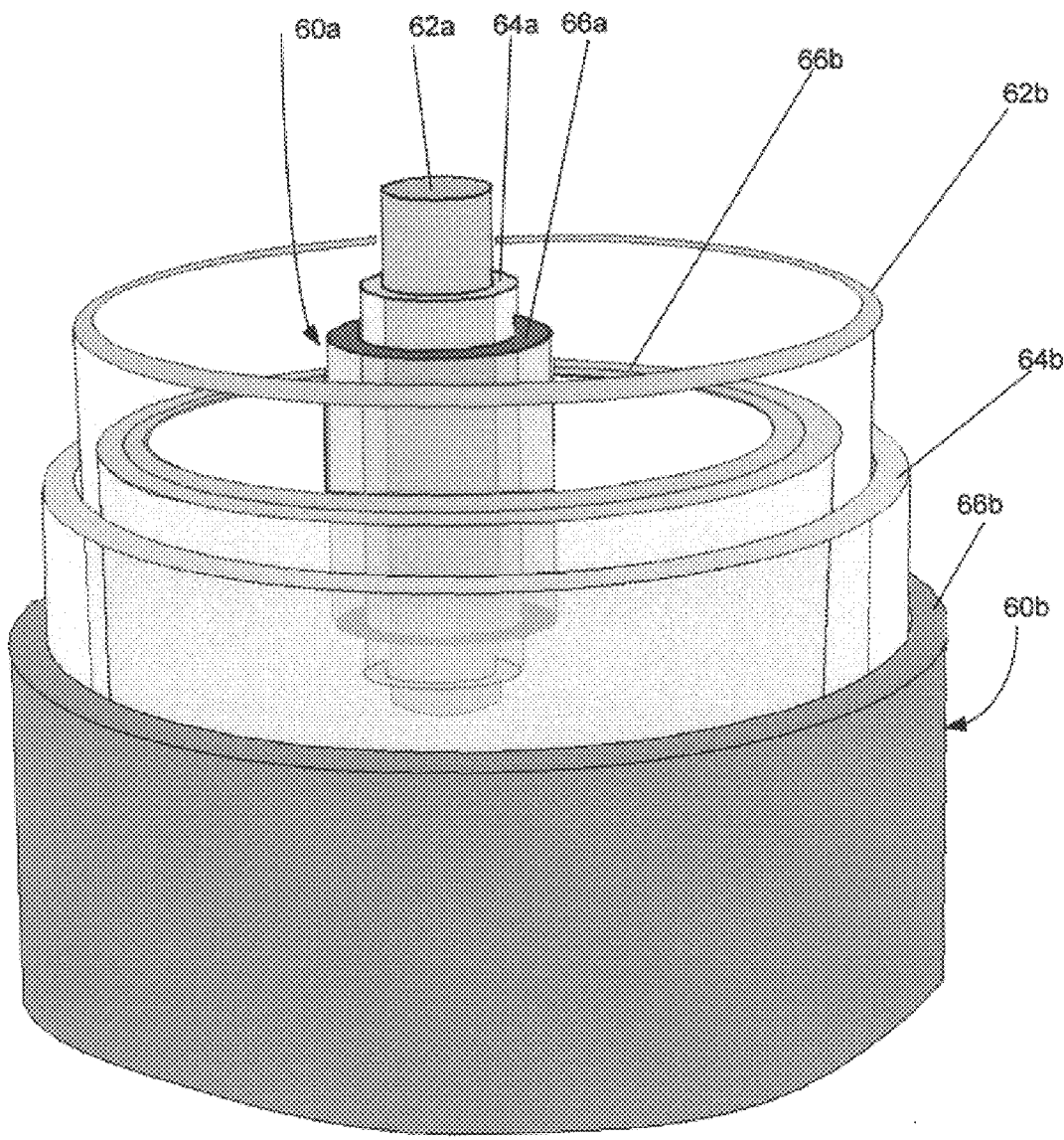
FIG. 6 is a cutaway view of two probes of the present invention wherein the probes are concentrically configured.

In yet another embodiment of the present invention, a pair of probes 60a and 60b is concentrically configured, as shown in FIG. 6. The inner probe 60a is rod-shaped, having an inner conducting element 62a that is covered with a dielectric layer 64a. An outer protective shell 66a encases both the inner conducting element 62a and the dielectric layer 64a. A ring-shaped probe 60b surrounds the rod-shaped probe 60a, with the two probes 60a, 60b being concentrically-located but separate. The ring-shaped probe 60b has an inner conducting element 62b that is surrounded by a dielectric layer 64b. An outer protective shell 66b encases both the inner conductor 62b and the dielectric layer 64b. In use the material to be measured in situated between the two probes 60a, 60b such that the material is lodged or flows between the two probes.

Figure 7:
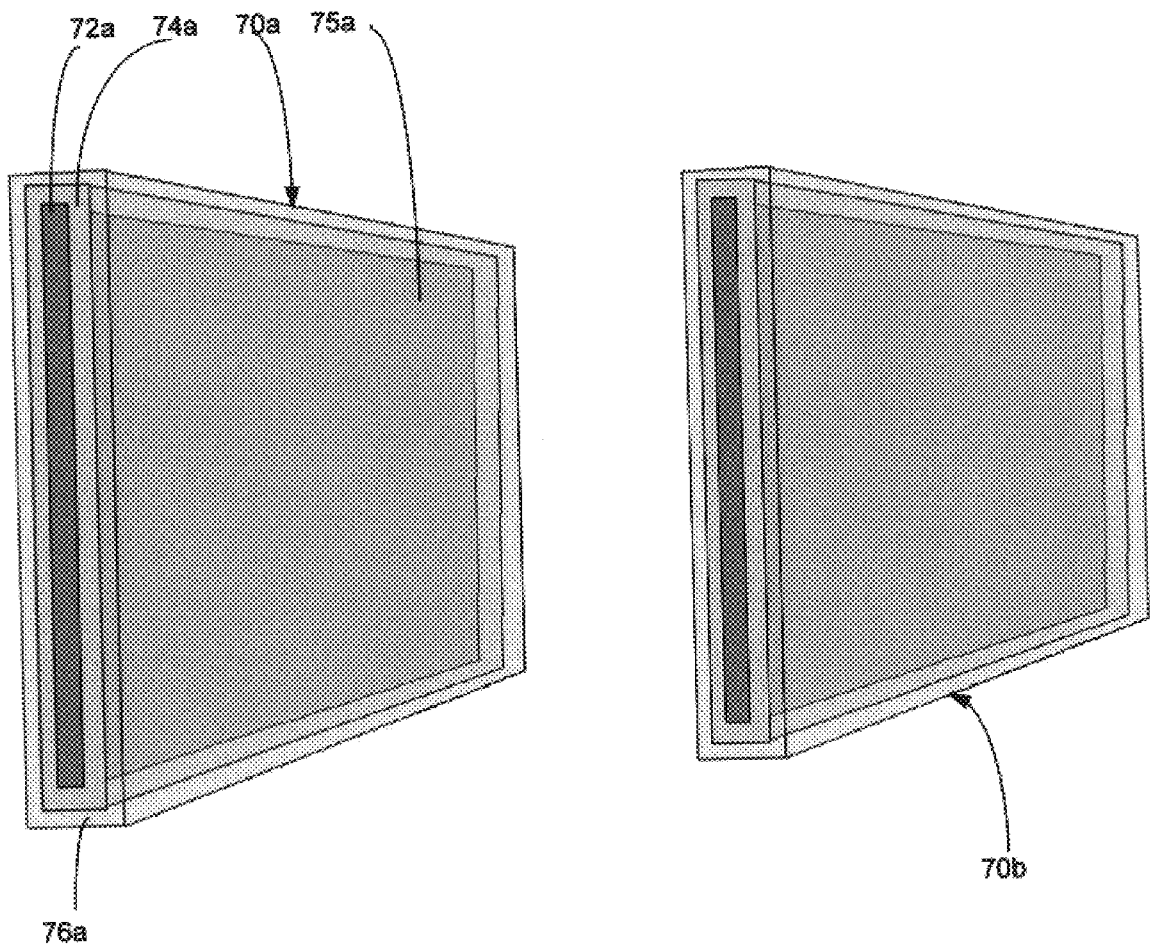
FIG. 7 is a cutaway view of two probes of the present invention wherein two rectangular plate-shaped probes are depicted.

In an embodiment of the probe of the present invention shown in FIG. 7, the probe 70a is plate-shaped. The probe 70a as a plate-shaped inner conductive element 72a that is surrounded by a dielectric layer 74a. The dielectric layer 74a is encased in a protective outer shell 76a. In use, two plate-shaped probes 70a, 70b can be configured such that they are parallel to each other and the material to be measured flows between the plated-shaped probes, along the larger surfaces of the probes (e.g., 75a). However, the probes 70a, 70b can also be configured such that they are closer to each other at one end and are further apart at the other end. This configuration might typically be used in a mixer or bulk transfer system where material flows between the probes and differing densities of the material to be measured may make it difficult to get accurate readings. Angling the probes 70a, 70b relative to each other in this manner increases the density of the material to be measured as it is compressed between the probes where the probes are least separated in distance. This increased density of the measured material allows for more accurate and consistent measurements of the dielectric properties of the materials. It should also be noted that the plate-shaped probes 70a, 70b in this embodiment do not necessarily have to be flat. These probes could be curved if desired. Additionally, the plate-shaped probes 70a, 70b do not have to be rectangular in shape. For instance, they could be circular, triangular or configured in any type of geometric cross-sectional shape.

Figure 8:
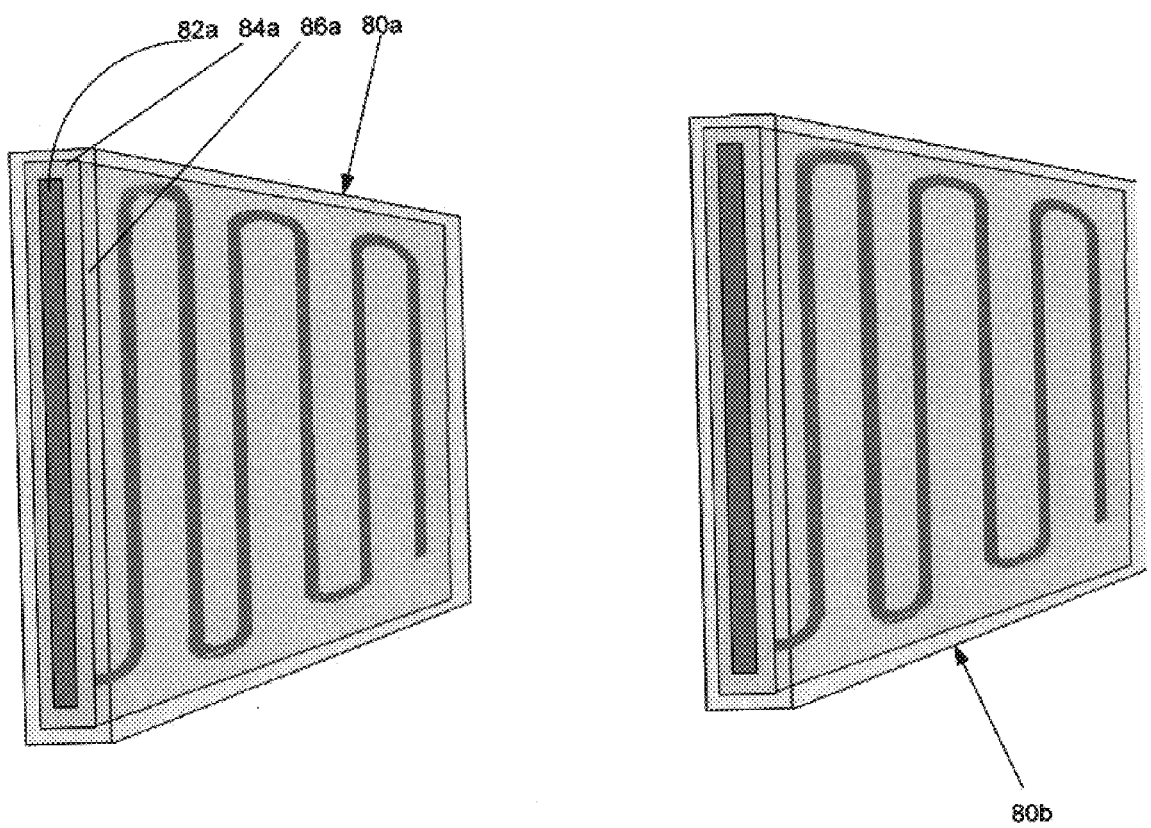
FIG. 8 is a cutaway view of two probes of the present invention wherein longer conductive elements are embedded in two rectangular plate-shaped probes.

In another embodiment of the probe of the present invention, shown in FIG. 8, a longer conductor is embedded within a plate-shaped probe 80a similar to that shown in FIG. 7. The longer conductor 82a, is a snake-like element encased in a dielectric material 84a. The conductor 82a and dielectric material 84a are covered by an outer protective shell 86a. Again, as discussed above in the embodiment depicted in FIG. 7, these probes 80a, 80b can be angled toward each other and can also be of different shapes (e.g., rectangular, circular, triangular, octagonal, etc.)

Materials

The probe of the present invention can be made of various materials. The inner conductive element is made of conductive material, typically a metal such as stainless steel or copper, for example. The dielectric layer that surrounds the inner conductive element of the probe of the present invention is typically hardenable epoxy of known dielectric constant. The outer protective shell is typically made of stainless steel, but could equally well be made of other materials that provide the desired protective effect.

While the invention has been described in detail by specific reference to preferred embodiments thereof, it is understood that variations and modifications thereof may be made without departing from the true spirit and scope of the invention. For example, probes of the present invention, using techniques described herein, can also be used in the following measurement areas:

(1) determination of concentrations of particles suspended in water and other liquids;
(2) determination of the amount of air entrapped in liquids, slurries and gels;
(3) determination of the liquid levels of immiscible fluids having differing dielectric character;
(4) determination of the proportional content in differing dielectrics soluble in water;
(5) and determination of the bulk content of the material being measured.

Wherefore, having thus described the present invention, what is claimed is:

1. A time domain reflectometry probe for measuring the dielectric properties of a material, comprising:

a center conductor, a dielectric material encasing said center conductor; and an outer conductive protective shell encasing both said center conductor and said dielectric material.

2. The time domain reflectometry probe of claim 1 wherein said probe is used for determining the moisture content in a material.

3. The time domain reflectometry probe of claim 1 wherein the outer protective shell is made of one of metal.

4. The time domain reflectometry probe of claim 1 wherein the outer protective shell is made of stainless steel.

5. The time domain reflectometry probe of claim 1 wherein the dielectric material encasing said center conductor is made of at least one of:

a gel of low dielectric constant;

a liquid of low dielectric constant; and a solid of low dielectric constant.

6. The time domain reflectometry probe of claim 1 wherein the dielectric material encasing said center conductor is made of at least one of:

epoxy;

plastic;

polycarbonate;

nylon; and oil.

7. The time domain reflectometry probe of claim 1 wherein, said probe is an elongated rod;

and wherein, said center conductor, said dielectric material encasing said center conductor and said outer protective shell encasing both said center conductor and said dielectric material are concentrically configured.

8. The time domain reflectometry probe of claim 1 wherein said probe has a cone-shaped tip.

9. The time domain reflectometry probe of claim 1 wherein, said probe is a rectangular plate;

and wherein, said center conductor is a rectangular plate, said dielectric material encases said center conductor and said outer protective shell encases both said center conductor and said dielectric material.

10. The time domain reflectometry probe of claim 9 wherein a pair of said probes is positioned parallel to each other such that a material to be measured flows between them.

11. The time domain reflectometry probe of claim 9 wherein a pair of said probes are positioned such that a material to be measured flows between them and that they are closer to each other at one end than the other such that the density of a material flowing between them is made more consistent so that more repeatable measurements can be taken.

12. The time domain reflectometry probe of claim 1 wherein,
said probe is a circular plate;
and wherein, said center conductor is a circular plate, said dielectric material encases said center conductor and said outer protective shell encases both said center conductor and said dielectric material.

13. The time domain reflectometry probe of claim 1 wherein,
said probe is a triangular plate;
and wherein, said center conductor is a triangular plate, said dielectric material encases said center conductor and said outer protective shell encases both said center conductor and said dielectric material.

14. The time domain reflectometry probe of claim 1 wherein,
said probe is rod-shaped, and wherein
said center conductor is coil-shaped; and wherein
said center conductor is potted in a dielectric material; and wherein
said outer protective shell encases said center conductor and said dielectric material.

15. The time domain reflectometry probe of claim 1 wherein,
said probe is disc-shaped having an annular hole through the center of the disc, and wherein
said center conductor said center conductor is a disc-shaped plate with an annular hole, said dielectric material encases said center conductor and said outer protective shell encases both said center conductor and said dielectric material.

16. The time domain reflectometry probe of claim 15 wherein said probe is mounted to a vehicle.

17. The time domain reflectometry probe of claim 1 wherein,
said probe is a rectangular plate; and wherein
said center conductor that snakes through the center of said rectangular plate; and wherein
said dielectric material encases said center conductor and said outer protective shell encases both said center conductor and said dielectric material.

18. The time domain reflectometry probe of claim 17 wherein a pair of said probes are positioned such that a material to be measured flows between them and that they are closer to each other at one end than the other such that the density of a material flowing between them is made more consistent so that more repeatable measurements can be taken.

19. A pair of time domain reflectometry probes for measuring the dielectric properties of a material, comprising:
a first rod-shaped probe, comprising
a center conductor,
a dielectric material encasing said center conductor; and
an outer protective shell encasing both said center conductor and said dielectric material; and
a second ring-shaped probe concentrically-located around said first probe, comprising:
a center conductor,
a dielectric material encasing said center conductor; and
an outer protective shell encasing both said center conductor and said dielectric material.

20. A probe for measuring the properties of a material, comprising:
a center conductor,
a dielectric material encasing said center conductor; and
an outer protective shell encasing both said center conductor and said dielectric material.

21. The probe of claim 19 wherein the probe is used in the measurement of at least one of:
(a) determination of concentrations of particles suspended in water and other liquids;
(b) determination of the amount of air entrapped in liquids, slurries and gels;
(c) determination of the liquid levels of immiscible fluids having differing dielectric character;
(d) determination of the proportional content in differing dielectrics soluble in water;
(d) and determination of the bulk content of the material being measured.

22. A method for using a time domain reflectometry probe assembly to measure the moisture content in a medium, comprising:
inserting a pair of probes of known length into a medium to be measured, wherein each probe comprises:
a center conductor,
a dielectric material encasing said center conductor; and
an outer protective shell encasing both said center conductor and said dielectric material;
connecting a coaxial cable to the pair of probes;
transmitting a signal of the kind used in time domain reflectometry through the coaxial cable and the probes;
introducing a detectable characteristic reference reflection into the signal by way of a specific construction-imposed impedance mismatch between the coaxial cable and the probes independent of the impedance of the medium being measured which causes an identifiable reference reflection in the signal transmitted through the probes in order to mark a known location in relation to the probes;
commencing a measurement of time delay in response to detection of the characteristic reference reflection;
calculating an apparent dielectric constant value based on the time delay; and
correlating the apparent dielectric constant with data reflecting the moisture content of the medium.

* * * * *